(12) United States Patent
Zhao et al.

(10) Patent No.: US 6,465,551 B1
(45) Date of Patent: *Oct. 15, 2002

(54) BICYCLO[2.2.1]HEPTANE DICARBOXYLATE SALTS AS POLYOLEFIN NUCLEATORS

(75) Inventors: Xiaodong Edward Zhao, Moore, SC (US); Darin L. Dotson, Spartanburg, SC (US)

(73) Assignee: Milliken & Company, Spartanburg, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/815,832

(22) Filed: Mar. 24, 2001

(51) Int. Cl.[7] .............................. C08K 5/09; C08K 5/12; C07C 69/74
(52) U.S. Cl. ........................ 524/284; 524/285; 560/120; 528/486
(58) Field of Search ................................. 524/284, 285; 560/120; 528/486

(56) References Cited

U.S. PATENT DOCUMENTS

| | | | | |
|---|---|---|---|---|
| 3,560,411 A | * | 2/1971 | Ruyter et al. | |
| 3,686,361 A | * | 8/1972 | De Witt, III et al. | |
| 4,647,581 A | * | 3/1987 | Kölbl et al. | |
| 5,047,574 A | * | 9/1991 | Ohtani et al. | |
| 5,922,793 A | | 7/1999 | Amos et al. | ................. 524/159 |
| 5,929,146 A | | 7/1999 | Amos et al. | ................... 524/89 |
| 5,981,636 A | | 11/1999 | Amos et al. | ................. 524/108 |
| 6,096,811 A | | 8/2000 | Amos et al. | ................... 524/89 |

* cited by examiner

*Primary Examiner*—Tae H. Yoon
(74) *Attorney, Agent, or Firm*—Terry T. Moyer; William S. Parks

(57) ABSTRACT

Compounds and compositions comprising specific metal salts of bicyclo[2.2.1]heptane dicarboxylate salts in order to provide highly desirable properties within polyolefin articles are provided. The inventive salts and derivatives thereof are useful as nucleating and/or clarifying agents for such polyolefin, provide excellent crystallization temperatures, stiffness, and calcium stearate compatibility within target polyolefin. Also, such compounds exhibit very low hygroscopicity and therefore excellent shelf stability as powdered or granular formulations. Polyolefin additive compositions and methods of producing polyolefin with such compounds are also contemplated within this invention.

21 Claims, No Drawings

BICYCLO[2.2.1]HEPTANE DICARBOXYLATE SALTS AS POLYOLEFIN NUCLEATORS

Field of the Invention

This invention relates to compounds and compositions comprising specific metal salts of bicyclo[2.2.1]heptane dicarboxylate salts in order to provide highly desirable properties within thermoplastic articles. The inventive salts and derivatives thereof are useful as nucleating and/or clarifying agents for such thermoplastics. Such compounds provide excellent crystallization temperatures, stiffness, and calcium stearate compatibility within target thermoplastics. Also, such compounds exhibit desirable migratory properties within thermoplastic articles and low hygroscopicity and therefore excellent shelf stability as powdered or granular formulations. Thermoplastic additive compositions and methods of producing thermoplastics with such compounds are also contemplated within this invention.

BACKGROUND OF THE PRIOR ART

All U.S. patents cited below are herein entirely incorporated by reference.

As used herein, the term "thermoplastic" is intended to mean a polymeric material that will melt upon exposure to sufficient heat but will retain its solidified state, but not prior shape without use of a mold or like article, upon sufficient cooling. Specifically, as well, such a term is intended solely to encompass polymers meeting such a broad definition that also exhibit either crystalline or semi-crystalline morphology upon cooling after melt-formation through the use of the aforementioned mold or like article. Particular types of polymers contemplated within such a definition include, without limitation, polyolefins (such as polyethylene, polypropylene, polybutylene, and any combination thereof), polyamides (such as nylon), polyurethanes, polyester (such as polyethylene terephthalate), and the like (as well as any combinations thereof).

Thermoplastics have been utilized in a variety of end-use applications, including storage containers, medical devices, food packages, plastic tubes and pipes, shelving units, and the like. Such base compositions, however, must exhibit certain physical characteristics in order to permit widespread use. Specifically within polyolefins, for example, uniformity in arrangement of crystals upon crystallization is a necessity to provide an effective, durable, and versatile polyolefin article. In order to achieve such desirable physical properties, it has been known that certain compounds and compositions provide nucleation sites for polyolefin crystal growth during molding or fabrication. Generally, compositions containing such nucleating compounds crystallize at a much faster rate than un-nucleated polyolefin. Such crystallization at higher temperatures results in reduced fabrication cycle times and a variety of improvements in physical properties, such as, as one example, stiffness.

Such compounds and compositions that provide faster and or higher polymer crystallization temperatures are thus popularly known as nucleators. Such compounds are, as their name suggests, utilized to provide nucleation sites for crystal growth during cooling of a thermoplastic molten formulation. Generally, the presence of such nucleation sites results in a larger number of smaller crystals. As a result of the smaller crystals formed therein, clarification of the target thermoplastic may also be achieved, although excellent clarity is not always a result. The more uniform, and preferably smaller, the crystal size, the less light is scattered. In such a manner, the clarity of the thermoplastic article itself can be improved. Thus, thermoplastic nucleator compounds are very important to the thermoplastic industry in order to provide enhanced clarity, physical properties and/or faster processing.

As an example of one type of nucleator, dibenzylidene sorbitol compounds are common nucleator compounds, particularly for polypropylene end products. Compounds such as 1,3-O-2,4-bis(3,4-dimethylbenzylidene) sorbitol (hereinafter DMDBS), available from Milliken Chemical under the trade name Millad® 3988, provide excellent nucleation characteristics for target polypropylenes and other polyolefins. Other well known compounds include sodium benzoate, sodium 2,2'-methylene-bis-(4,6-di-tert-butylphenyl) phosphate (from Asahi Denka Kogyo K.K., known as NA-11), talc, and the like. Such compounds all impart high polyolefin crystallization temperatures; however, each also exhibits its own drawback for large-scale industrial applications.

Other acetals of sorbitol and xylitol are typical nucleators for polyolefins and other thermoplastics as well. Dibenzylidene sorbitol (DBS) was first disclosed in U.S. Pat. No. 4,016,118 by Hamada, et al. as an effective nucleating and clarifying agents for polyolefin. Since then, large number of acetals of sorbitol and xylitol have been disclosed. Representative US patents include: Kawai, et al., U.S. Pat. No. 4,314,039 on di(alkylbenzylidene) sorbitols; Mahaffey, Jr., U.S. Pat. No. 4,371,645 on di-acetals of sorbitol having at least one chlorine or bromine substituent; Kobayashi, et al., U.S. Pat. No. 4,532,280 on di(methyl or ethyl substituted benzylidene) sorbitol; Rekers, U.S. Pat. No. 5,049,605 on bis(3,4-dialkylbenzylidene) sorbitols including substituents forming a carbocyclic ring.

Another example of the effective nucleating agents are the metal salts of organic acids. Wijga in U.S. Pat. Nos. 3,207,735, 3,207,736, and 3,207,738, and Wales in U.S. Pat. Nos. 3,207,737 and 3,207,739, all patented Sept. 21, 1966, suggest that aliphatic, cycloaliphatic, and aromatic carboxylic, dicarboxylic or higher polycarboxylic acids, corresponding anhydrides and metal salts are effective nucleating agents for polyolefin. They further state that benzoic acid type compounds, in particular sodium benzoate, are the best embodiment of the nucleating agents.

Another class of nucleating agents, alluded to above, was suggested by Nakahara, et al. in U.S. Pat. No. 4,463,113, in which cyclic bis-phenol phosphates was disclosed as nucleating and clarifying agents for polyolefin resins. Kimura, et al. then suggests in U.S. Pat. No. 5,342,868 that the addition of an alkali metal carboxylate to basic polyvalent metal salt of cyclic organophosphoric ester can further improve the clarification effects of such additives. Compounds that are based upon this technologies are marketed under the trade name NA-11 and NA-21.

Furthermore, a certain class of bicyclic compounds, such as bicyclic dicarboxylic acid and salts, have been taught as polyolefin nucleating agents as well within Patent Cooperation Treaty Application WO 98/29494, to Minnesota Mining and Manufacturing. The best working example of this technology is embodied in disodium bicyclo[2.2.1]heptene dicarboxylate and formulations with such compounds.

Such compounds all impart relatively high polyolefin crystallization temperatures; however, each also exhibits its own drawback for large-scale industrial applications.

For example, of great interest is the compatibility of such compounds with different additives widely used within typical polyolefin (e.g., polypropylene, polyethylene, and the like) plastic articles. For instance, calcium stearate is a very popular acid neutralizer present within typical polypropylene formulations to protect the end product from catalyst residue attack. Unfortunately, most of the nucleator compounds noted above exhibit deleterious reactions with such compounds within polyolefin articles. For sodium, and other like metal ions, it appears that the calcium ion from the stearate transfers positions with the sodium ions of the nucleating agents, rendering the nucleating agents ineffective for their intended function. As a result, such compounds sometimes exhibit unwanted plate-out characteristics and overall reduced nucleation performance (as measured, for example) by a decrease in crystallization temperature during and after polyolefin processing. Other processing problems are evident with such compounds as well.

Other problems encountered with the standard nucleators noted above include inconsistent nucleation due to dispersion problems, resulting in stiffness and impact variation in the polyolefin article. Substantial uniformity in polyolefin production is highly desirable because it results in relatively uniform finished polyolefin articles. If the resultant article does not contain a well-dispersed nucleating agent, the entire article itself may suffer from a lack of rigidity and low impact strength.

Furthermore, storage stability of nucleator compounds and compositions is another potential problem with thermoplastic nucleators and thus is of enormous importance as well. Since nucleator compounds are generally provided in powder or granular form to the polyolefin manufacturer, and since uniform small particles of nucleating agents is imperative to provide the requisite uniform dispersion and performance, such compounds must remain as small particles through storage. Certain nucleators, such as sodium benzoate, exhibit high degrees of hygroscopicity such that the powders made therefrom hydrate easily resulting in particulate agglomeration. Such agglomerated particles may require further milling or other processing for deagglomeration in order to achieve the desired uniform dispersion within the target thermoplastic. Furthermore, such unwanted agglomeration due to hydration may also cause feeding and/or handling problems for the user.

Also of great interest is the compatibility of such compounds with different additives widely used within typical polyolefin (e.g., polypropylene, polyethylene, and the like) plastic articles. As noted previously, calcium stearate compatibility is particularly important. Unfortunately, most of the nucleators compounds noted above (such as sodium benzoate, NA-11, disodium bicyclo[2.2.1] heptene dicarboxylate) exhibit much deleterious nucleating efficacy with such compounds within polyolefin articles. In order to avoid combinations of these standard nucleators and calcium salts, other nonionic acid neutralizers, such as dihydrotalcite (DHT4-A), would be necessary for use in conjunction with such nucleators. Such a combination, however, has proven problematic in certain circumstances due to worsened aesthetic characteristics (e.g., higher haze), and certainly higher costs in comparison with standard calcium salts.

Some nucleating agents, such as certain DBS derivatives, exhibit certain practical deficiencies such as a tendency to plate-out at high processing temperatures. DBS derivatives, particularly where the aromatic rings are mono-substituted, show much improved thermal stability. However, such compounds also tend to exhibit undesirable migratory properties coupled with problematic organoleptic deficiencies within certain polyolefin articles. As a result, such compounds are limited in their practical in some important areas, such as medical device packaging.

These noticeable problems have thus created a long-felt need in the polyolefin nucleator compound industry to provide such compounds that do not exhibit the aforementioned problems and provide excellent peak crystallization temperatures for the target polyolefin themselves. To date, the best compounds for this purpose remain those noted above. Unfortunately, nucleators exhibiting exceptionally high peak crystallization temperatures, low hygroscopicity, excellent thermal stability, and non-migratory properties within certain target polyolefin, and compatibility with most standard polyolefin additives (such as, most importantly, calcium stearate) have not been accorded the polyolefin nucleator industry.

OBJECTS OF THE INVENTION

Therefore, an object of the invention is to provide a polyolefin nucleating agent that exhibit exceptional nucleation efficacy as indicated by exceptional high polymer peak crystallization temperatures within polyolefin articles. A further object of the invention is to provide a nucleating compound and compositions thereof that exhibit excellent calcium stearate compatibility within target polyolefin articles and formulations. Another objective of this invention is to provide formulations that exhibit extremely low hygroscopicity in order to accord an extremely good shelf-stable additive composition. Yet another object of this invention is to provide nucleating and clarifying compounds and compositions that exhibit exceptional thermal stability and non-migratory properties. Yet another object of the invention is to provide nucleating compounds that within the target polyolefin articles exhibit excellent mechanical properties. Additionally, it is an object of this invention to provide nucleating compounds or compositions that may be used in various polyolefin media for use in myriad end-uses.

Accordingly, this invention encompasses a saturated metal or organic salts of bicyclic dicarboxylates, preferably, bicyclo[2.2.1]heptane-dicarboxylates, and most preferably of a compound conforming to Formula (I)

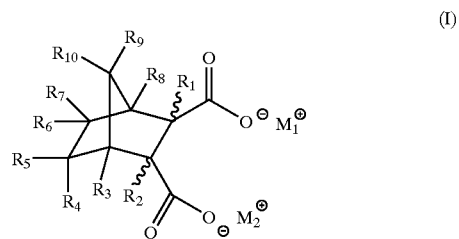

(I)

wherein $M_1$ and $M_2$ are the same or different and are independently selected from the group consisting of metal or organic cations, and $R_1$, $R_2$, $R_3$, $R_4$, $R_5$, $R_6$, $R_7$, $R_8$, $R_9$, and $R_{10}$ are individually selected from the group consisting of hydrogen, $C_1$–$C_9$ alkyl, hydroxy, $C_1$–$C_9$ alkoxy, $C_1$–$C_9$ alkyleneoxy, amine, and $C_1$–$C_9$ alkylamine, halogen, phenyl, alkylphenyl, and geminal or vicinal $C_1$–$C_9$ carbocyclic. Preferably, the metal cations are selected from the group consisting of calcium, strontium, barium, magnesium, aluminum, silver, sodium, lithium, rubidium, potassium, and the like. Within that scope, group I and group II metal ions are generally preferred. Among the group I and II cations, sodium, potassium, calcium and strontium are preferred, wherein sodium and calcium are most preferred. Furthermore, the $M_1$ and $M_2$ groups may also be combined to form a single metal cation (such as calcium, strontium, barium, magnesium, aluminum, including monobasic aluminum, and the like). Although this invention encompasses all stereochemical configurations of such compounds, the cis configuration is preferred wherein cis-endo is the most preferred embodiment. The preferred embodiment polyolefin articles and additive compositions for polyolefin formulations comprising at least one of such compounds, broadly stated as saturated bicyclic carboxylate salts, are also encompassed within this invention.

DETAILED DESCRIPTION OF THE INVENTION

As noted above, in order to develop a proper polyolefin nucleator compound or composition for industrial applications, a number of important criteria needed to be met. The inventive nucleating agents meet all of these important requirements very well. For instance, as discussed in greater detail below, these inventive salts provide excellent high peak crystallization temperatures in a variety of polyolefin formulations, particularly within random copolymer polypropylene (hereinafter RCP) and homopolymer polypropylene (hereinafter HP). As a result, such inventive salts provide excellent mechanical properties for polyolefin articles without the need for extra fillers and rigidifying additives, and desirable processing characteristics such as improved (shorter) cycle time. The salts also show much improved hygroscopicity comparing to prior art and thus granular or powder formulations of such a salt do not agglomerate or clump together. Lastly, such inventive salts do not interact deleteriously with calcium stearate additives.

Such properties are highly unexpected and unpredictable, particularly in view of the closest prior art, the WO 98/29494 reference discloses nucleation and clarification additives for polyolefin articles including unsaturated [2.2.1] dicarboxylate salts; however, there is no exemplification of a saturated dicarboxylate salt of this type. The closest embodiment within that art is identified as disodium bicyclo[2.2.1] heptene dicarboxylate. After intensive investigations, it has been determined that, quite unexpectedly, as discussed below in greater detail, the hydrogenation of such compounds provides vastly improved nucleation efficacy for the inventive compounds and within the inventive polyolefin compositions. It has now been found that the saturation of Diels-Alder reaction products to form dicarboxylate salts, and in particular, without intending to limit the scope of the invention, saturated bicyclic dicarboxylate salts, provide unforeseen benefits for polyolefin nucleation processes.

As indicated in Table 1, below, the peak crystallization temperatures provided target polyolefin articles with these inventive saturated compounds are from about 2.5 to about 5° C. above that for the related unsaturated compounds. Such dramatic improvements are simply unexpected and are unpredictable from any known empirical or theoretical considerations. Furthermore, significant improvements in hygroscopicity of the saturated compounds were also unexpectedly observed. Such unpredictable improvements are of great practical significance as discussed before.

Yet another surprise was the improved compatibility between these inventive saturated compounds and typical acid scavenger salt compounds utilized within polyolefin formulations and articles, such as calcium and lithium stearate. Such compatibility, coupled with the high peak crystallization temperatures available from the inventive compounds, thus provides a highly desirable thermoplastic nucelator compound. The inventive salts are thus added within the target polyolefin in an amount from about 50 ppm to about 20,000 pm by weight in order to provide the aforementioned beneficial characteristics, most preferably from about 200 to about 4000 ppm. Higher levels, e.g., 50% or more by weight, may also be used in a masterbatch formulation. Optional additives within the inventive salt-containing composition, or within the final polyolefin article made therewith, may include plasticizers, antistatic agents, stabilizers, ultraviolet absorbers, and other similar standard polyolefin thermoplastic additives. Other additives may also be present within this composition, most notably plasticizers, acid scavengers, antimicrobials (preferably silver-based ion-exchange compounds, such as ALPHASAN® antimicrobials available from Milliken & Company), antioxidants, flame retardants, light stabilizers, antistatic agents, colorants, pigments, perfumes, chlorine scavengers, and the like.

The term polyolefin or polyolefin resin is intended to encompass any materials comprised of at least one polyolefin compound. Preferred examples include isotactic and syndiotactic polypropylene, polyethylene, poly(4-methyl) pentene, polybutylene, and any blends or copolymers thereof, whether high or low density in composition. The polyolefin polymers of the present invention may include aliphatic polyolefins and copolymers made from at least one aliphatic olefin and one or more ethylenically unsaturated co-monomers. Generally, the co-monomers, if present, will be provided in a minor amount, e.g., about 10 percent or less or even about 5 percent or less, based upon the weight of the polyolefin (e.g. random copolymer polypropylene), but copolymers containing up to 25% or more of the co-monomer (e.g., impact copolymers) are also envisaged. Other polymers or rubber (such as EPDM or EPR) may also be compounded with the polyolefin to obtain the aforementioned characteristics. Such co-monomers may serve to assist in clarity improvement of the polyolefin, or they may function to improve other properties of the polymer. Other examples include acrylic acid and vinyl acetate, etc. Examples of olefin polymers whose transparency can be improved conveniently according to the present invention are polymers and copolymers of aliphatic monoolefins containing 2 to about 6 carbon atoms which have an average molecular weight of from about 10,000 to about 2,000,000, preferably from about 30,000 to about 300,000, such as, without limitation, polyethylene, linear low density polyethylene, isotactic polypropylene, syndiotactic polypropylene, crystalline ethylenepropylene copolymer, poly(1-butene), polymethylpentene, 1-hexene, 1-octene, and vinyl cyclohexane. The polyolefins of the present invention may be described as basically linear, regular polymers that may optionally contain side chains such as are found, for instance, in conventional low density polyethylene.

Although polyolefins are preferred, the nucleating agents of the present invention are not restricted to polyolefins, and may also give beneficial nucleation properties to polyesters such as polyethylene terephthalate (PET), polybutylene terephthalate (PBT), and polyethylene naphthalate (PEN), as well as polyamides such as Nylon 6, Nylon 6,6, and others. Generally, any thermoplastic composition having some crystalline content may be improved with the nucleating agents of the present invention.

The compositions of the present invention may be obtained by adding the inventive saturated bicyclic dicarboxylic salt (or combination of salts or composition comprising such salts) to the thermoplastic polymer or copolymer and merely mixing the resultant composition by any suitable means. Alternatively, a concentrate containing as much as about 20 percent by weight of the inventive saturated [2.2.1] salt in a polyolefin masterbatch comprising the required acid scavenger may be prepared and be subsequently mixed with the target resin. Furthermore, the inventive compositions (with other additives potentially) may be present in any type of standard thermoplastic (e.g., polyolefin, most preferably) additive form, including, without limitation, powder, prill, agglomerate, liquid suspension, and the like, particularly comprising dispersion aids such as polyolefin (e.g., polyethylene) waxes, stearate esters of glycerin, montan waxes, mineral oil, and the like. Basically, any form may be exhibited by such a combination or composition including such combination made from blending, agglomeration, compaction, and/or extrusion.

The composition may then be processed and fabricated by any number of different techniques, including, without limitation, injection molding, injection blow molding, injection stretch blow molding, injection rotational molding, extrusion, extrusion blow molding, sheet extrusion, film extrusion, cast film extrusion, foam extrusion, thermoforming (such as into films, blown-films, biaxially oriented films), thin wall injection molding, and the like into a fabricated article.

Preferred Embodiments of the Invention

This invention can be further elucidated through the following examples where examples of particularly preferred embodiment within the scope of the present invention are presented.

Production of Inventive Salts

EXAMPLE 1

Disodium Bicyclo[2.2.1]heptane-2,3-dicarboxylate

To a solution of disodium bicyclo[2.2.1]hept-5-ene-2,3-dicarboxylate (10.0 g, from example 3) in water (100 g) was added 0.5 g palladium on activated carbon (5 wt %). The mixture was transferred into a Parr reactor and was subjected to hydrogenation (50 psi, room temperature) for 8 hours. The activated carbon was filtered out, and the water was removed in vacuo at 75° C. The resulting product was dried and milled (m.p >300° C.). NMR and IR analyses were consistent with that of the expected structure.

EXAMPLE 2

Calcium Bicyclo[2.2.1]heptane-2,3-dicarboxyl ate

To a solution of disodium bicyclo[2.2.1]heptane-2,3-dicarboxylate (22.6 g, 0.1 mols) in water (150 g) was added a solution of calcium chloride dihydrate (14.7 g, 0. 1 mols) in water (100 g). The mixture was stirred at 60° C. for 2 hours. The resulting white precipitate was filtered. The white powdery product was dried and milled (m.p. >300° C.).

Other Group I and II salts, lithium, potassium, rubidium, magnesium, strontium, and barium salts of bicyclo[2.2.1] heptane dicarboxylates were synthesized through similar procedures of reacting a Group I or II salt with disodium bicyclo[2.2.1]heptane-2,3-dicarboxylate.

EXAMPLE 3 (Comparative)

Disodium bicyclo[2.2.1]hept-5-ene-2,3-dicarboxylate

To a suspension of endo-bicyclo[2.2.1]hept-5-ene-2,3-dicarboxylic anhydride (16.4 g, 0.1 mols) in water (100 g) was added sodium hydroxide (8.0 g, 0.2 mols) at room temperature. The mixture was then stirred at 80° C. for 2 hours. A clear, homogeneous solution was obtained. Water was removed in vacuum at 75° C. and the resulting white crystalline product was dried and milled (m.p. >300 C).

Other comparative examples of commercial samples of Millad® 3988, sodium benzoate, NA-11, and NA-21 were used in this evaluation as well.

Nucleation Efficacy Test:

Thermoplastic compositions (plaques) were produced comprising the additives from the Examples above and sample homopolymer polypropylene (HP) resin plaques, produced dry blended in a Welex mixer at ~2000 rpm, extruded through a single screw extruder at 400–450° F., and pelletized. Accordingly, one kilogram batches of target polypropylene were produced in accordance with the following table:

| HOMOPOLYMER POLYPROPYLENE COMPOSITION TABLE | |
| --- | --- |
| Component | Amount |
| Polypropylene homopolymer (Himont Profax ® 6301) | 1000 g |
| Irganox ® 1010, Primary Antioxidant (from Ciba) | 500 ppm |
| Irgafos ® 168, Secondary Antioxidant (from Ciba) | 1000 ppm |
| Calcium Stearate, Acid Scavenger | 800 ppm |
| Inventive Nucleator | as noted |

The base HP and all additives were weighed and then blended in a Welex mixer for 1 minute at about 1600 rpm. All samples were then melt compounded on a Killion single screw extruder at a ramped temperature from about 204° to 232° C. through four heating zones. The melt temperature upon exit of the extruder die was about 246° C. The screw had a diameter of 2.54 cm and a length/diameter ratio of 24:1. Upon melting the molten polymer was filtered through a 60 mesh (250 micron) screen. Plaques of the target polypropylene were then made through extrusion into an Arburg 25 ton injection molder. The molder molder was set at a temperature anywhere between 190 and 260° C., with a range of 190 to 240° C. preferred, most preferably from about 200 to 230° C. The plaques had dimensions of about 51 mm×76 mm×1.27 mm, and the mold had a mirror finish which was transferred to the individual plaques. The mold cooling circulating water was controlled at a temperature of about 25° C.

Testing for nucleating effects and other important criteria were accomplished through the formation of plaques of clarified polypropylene thermoplastic resin. These plaques were formed through the process outlined above with the specific compositions listed above in the above Table.

These plaque formulations are, of course, merely preferred embodiments of the inventive article and method and are not intended to limit the scope of this invention. The resultant plaques were then tested for peak crystallization temperatures (by Differential Scanning Calorimetry). Crystallization is important in order to determine the time needed to form a solid article from the molten polyolefin composition. Generally, a polyolefin such as polypropylene has a crystallization temperature of about 110° C. at a cooling rate of 20° C./min. In order to reduce the amount of time needed to form the final product, as well as to provide the most effective nucleation for the polyolefin, the best nucleator compound added will invariably also provide the highest crystallization temperature for the final polyolefin product. The nucleation composition efficacy, particular polymer peak crystallization temperature ($T_c$), was evaluated by using DSC according to ASTM D-794-85. To measure these temperatures, the specific polypropylene composition was heated from 60° C. to 220° C. at a rate of 20° C. per minute to produce a molten formulation and held at the peak temperature for 2 minutes. At that time, the temperature was then lowered at a rate of 20° C. per minute until it reached the starting temperature of 60° C. The crystallization temperature was thus measured as the peak maximum during the crystallization exotherm. The clarification performance of the nucleators was measured using ASTM D 1003-92.

The following Table lists the peak crystallization temperatures for the plaques prepared above:

EXPERIMENTAL TABLE 1
Performance of Bicyclic Nucleators in Polypropylene Homopolymer

| Additives | Additive Conc. (%) | Polym. Cryst. Temp | % Haze |
|---|---|---|---|
| Example 1 | 0.1 | 126 | 34% |
| Example 1 | 0.25 | 128 | 30% |
| Example 2 | 0.1 | 125 | 48% |
| Example 2 | 0.25 | 127 | 45% |
| Lithium bicyclo-[2.2.1]heptane dicarboxylate | 0.25 | 123 | 56% |
| Potassium bicyclo-[2.2.1]heptane dicarboxylate | 0.25 | 125 | 67% |
| Rubidium bicyclo-[2.2.1]heptane dicarboxylate | 0.25 | 123 | 55% |
| Magnesium bicyclo-[2.2.1]heptane dicarboxylate | 0.25 | 117 | 78% |
| Barium bicyclo-[2.2.1]heptane dicarboxylate | 0.25 | 121 | 71% |
| Strontium bicyclo-[2.2.1]heptane dicarboxylate | 0.25 | 124 | 56% |
| None | | 110 | 68% |
| Example 3 | 0.1 | 122 | 50% |
| Example 3 | 0.25 | 123 | 46% |
| DMDBS | 0.25 | 123 | 11% |
| Na-11 | 0.1 | 124 | 32% |
| Na-21 | 0.25 | 123 | 20% |

The data shows that inventive products in example 2 and example 3 exhibit significantly higher polymer peak crystallization temperature and lower haze.

Another important test for nucleation efficacy is the crystallization half-time (T½). This measurement was conducted on DSC where the specific polypropylene composition was heated from 60° C. to 220° C. at a rate of 20° C. per minute to produce a molten formulation and held at the peak temperature for 2 minutes. At that time, the temperature was then lowered quickly to 140° C., where the sample was held. The exotherm of crystallization was measured with time. The time where exactly one-half of the heat of crystallization is generated was recorded as the crystallization half time. Shorter crystallization half time is indicative of higher nucleation efficacy. In a practical sense, a shorter crystallization half time is an indicator of a shorter cycle time, and thus of significant value.

EXPERIMENTAL TABLE 2
Crystallization Half Time in Homopolymer

| Additives | Loading (%) | T1/2 (minutes) |
|---|---|---|
| Example 3 | 0.25 | 4.50 |
| Example 1 | 0.25 | 0.98 |
| Example 2 | 0.25 | 1.40 |

The data shows that the inventive compounds in Example 1 and Example 2 exhibit significantly shorter crystallization half time.

Calcium Stearate Compatibility Test:

In this test, the nucleators were tested in formulations with and without calcium stearate. The nucleation efficacy of the nucleators in each formulation was studied by measuring polymer crystallization temperature. The formulations and testing conditions are identical with those discussed above. A drop of 2° C. or more is considered a failure.

EXPERIMENTAL TABLE 3
Calcium Stearate Compatibility Test

| Additives | Loading (%) | Loading of CaSt (%) | Polym. Peak Crys. Temp. (° C.) |
|---|---|---|---|
| Example 2 | 0.25 | 0 | 128 |
| Example 2 | 0.25 | 0.08 | 128 |
| Example 3 | 0.25 | 0 | 127 |
| Example 3 | 0.25 | 0.08 | 127 |
| NA-11 | 0.1 | 0.08 | 124 |
| NA-11 | 0.1 | 0.08 | 121 |
| Example 1 | 0.25 | 0 | 123 |
| Example 1 | 0.25 | 0.08 | 121 |

The data shows that only the inventive nucleators in Example 1 and Example 2 pass the compatibility test with calcium stearate.

Hygroscopicity Test:

These tests were carried out on the milled products to give adequate surface area for moisture uptake. Two grams of each example were spread out on a watch glass and weighed immediately after drying in a vacuum oven. The samples were then placed in a controlled humidity (65%) environment and the weight was taken each day for 7 days. The percent weight gain was defined as the percent moisture uptake. Table 5 below summarizes the results:

EXPERIMENTAL TABLE 4
Hygroscopicity Test Data

| Entry | Sample | Weight Gain (% w/w) |
|---|---|---|
| 1 | Example 3 | 8% |
| 2 | Example 1 | 1% |
| 3 | Example 2 | 0% |

It is clear from the above data that saturation of Example 3 reduces the hygroscopicity over that of the prior art significantly, and the use of calcium as the metal reduces the moisture uptake to zero.

Nucleation Efficacy in Polyester:

The inventive additives were also tested as nucleating agents for polyester. Additives were compounded with a C.W. Brabender Torque Rheometer at 5000 ppm into Shell Cleartuff™ 8006 PET bottle grade resin having an IV of 0.80. All resin was dried to than 20 ppm water. Samples were taken, pressed, and rapidly cooled into 20–40 mil films. All samples were dried at 150° C. under vacuum for 6 h prior to analysis. The samples were analyzed under nitrogen on a Perkin Elmer System 7 differential scanning calorimeter using a heating and cooling rate of 20° C./min. The polymer peak cristalization temperature was measured as described before. The data is shown in Table 6 below:

EXERIMENTAL TABLE 5
Polyester Nucleating Results

| Sample | Peak Cryst. Temp. (° C.) |
|---|---|
| Control | 155 |
| Example 3 | 184 |
| Example 1 | 194 |

Thus, the inventive saturated compound exhibited much improved nucleation of polyester over the control with no nucleator compound and the unsaturated nucleator compound.

Having described the invention in detail it is obvious that one skilled in the art will be able to make variations and modifications thereto without departing from the scope of the present invention. Accordingly, the scope of the present invention should be determined only by the claims appended hereto.

That which is claimed is:

1. A thermoplastic article comprising at least one compound conforming to the structure of Formula (I)

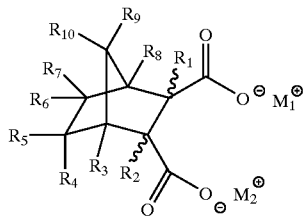

(I)

wherein $M_1$ and $M_2$ are the same or different, such that $M_1$ and $M_2$ may individually constitute monovalent cations, or $M_1$ and $M_2$ may be combined to form a single multivalent cation; wherein $M_1$ and $M_2$ are independently selected from the group consisting of at least one metal cation and at least one organic cation, and $R_1$, $R_2$, $R_3$, $R_4$, $R_5$, $R_6$, $R_7$, $R_8$, $R_9$, and $R_{10}$ are individually selected from the group consisting of hydrogen, $C_1$–$C_9$ alkyl, hydroxy, $C_1$–$C_9$ alkoxy, $C_1$–$C_9$ alkyleneoxy, amine, $C_1$–$C_9$ alkylamine, halogen, phenyl, alkylphenyl, and geminal or vicinal $C_1$–$C_9$ carbocyclic.

2. The thermoplastic article of claim 1 wherein said at least one metal cation is present and is selected from the group consisting of Group I and Group II metal ions.

3. The thermoplastic article of claim 2 wherein $M_1$ and $M_2$ are the same monovalent cation selected from the group consisting of sodium, potassium, lithium, rubidium, and silver.

4. The thermoplastic article of claim 2 wherein $M_1$ and $M_2$ are combined into a single multivalent cation selected from the group consisting of magnesium, calcium, strontium, barium, zinc, and aluminum.

5. The thermoplastic article of claim 3 wherein $M_1$ and $M_2$ are both sodium.

6. The thermoplastic article of claim 4 wherein said single moiety is calcium.

7. The thermoplastic article of claim 1 comprising a thermoplastic selected from the group consisting of at least one polyolefin and at least one polyester.

8. The thermoplastic article of claim 2 comprising a thermoplastic selected from the group consisting of at least one polyolefin and at least one polyester.

9. The thermoplastic article of claim 3 comprising a thermoplastic selected from the group consisting of at least one polyolefin and at least one polyester.

10. The thermoplastic article of claim 4 comprising a thermoplastic selected from the group consisting of at least one polyolefin and at least one polyester.

11. The thermoplastic article of claim 5 comprising a thermoplastic selected from the group consisting of at least one polyolefin and at least one polyester.

12. The thermoplastic article of claim 6 comprising a thermoplastic selected from the group consisting of at least one polyolefin and at least one polyester.

13. A polymer additive composition comprising at least one compound conforming to the structure of Formula (I)

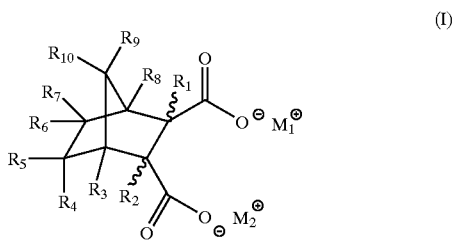

(I)

wherein $M_1$ and $M_2$ are the same or different, such that $M_1$ and $M_2$ may individually constitute monovalent cations, or $M_1$ and $M_2$ may be combined to form a single multivalent cation; wherein $M_1$ and $M_2$ are independently selected from the group consisting of at least one metal cation and at least one organic cation, and $R_1$, $R_2$, $R_3$, $R_4$, $R_5$, $R_6$, $R_7$, $R_8$, $R_9$, and $R_{10}$ are individually selected from the group consisting of hydrogen, $C_1$–$C_9$ alkyl, hydroxy, $C_1$–$C_9$ alkoxy, $C_1$–$C_9$ alkyleneoxy, amine, $C_1$–$C_9$ alkylamine, halogen, phenyl, alkylphenyl, and geminal or vicinal $C_1$–$C_9$ carbocyclic; wherein said additive composition is present in a form selected from the group consisting of a powder, a pellet, and a liquid, and wherein said composition also comprises at least one polymer, and, optionally, at least one compound selected from the group consisting of plasticizers, acid scavengers, antioxidants, antimicrobials, flame retardants, light stabilizers, antistatic agents, colorants, pigments, and any combination thereof.

14. The polymer additive composition of claim 13 wherein said at least one metal cation is present and is selected from the group consisting of Group I and Group II metal ions.

15. The thermoplastic article of claim 14 wherein $M_1$ and $M_2$ are the same monovalent cation selected from the group consisting of sodium, potassium, lithium, rubidium, and silver.

16. The thermoplastic article of claim 14 wherein $M_1$ and $M_2$ are combined into a single multivalent cation selected from the group consisting of magnesium, calcium, strontium, barium, zinc, and aluminum.

17. The thermoplastic article of claim 15 wherein $M_1$ and $M_2$ are both sodium.

18. The thermoplastic article of claim 16 wherein said single moiety is calcium.

19. A thermoplastic article comprising at least one saturated bicyclo 2.2.1heptane dicarboxylate salt compound.

20. The thermoplastic article of claim 19, wherein said thermoplastic comprises a polyolefin.

21. The thermoplastic article of claim 19 wherein said thermoplastic comprises a polyester.

* * * * *